United States Patent [19]

Schiller et al.

[11] Patent Number: 5,597,882
[45] Date of Patent: Jan. 28, 1997

[54] TIN COMPOUND-CONTAINING COMPOSITIONS AS ONE OF THE TWO COMPONENTS OF TWO COMPONENT SYSTEMS WHICH CROSSLINK AT ROOM TEMPERATURE TO GIVE ORGANOPOLYSILOXANE ELASTOMERS

[75] Inventors: August Schiller, Neuoetting; Norman Dorsch, Burghausen; Werner Graf, Burghausen; Alois Strasser, Burhgausen, all of Germany

[73] Assignee: Wacker-Chemie GmbH, Munich, Germany

[21] Appl. No.: 240,742

[22] Filed: Sep. 6, 1994

[30] Foreign Application Priority Data

Nov. 15, 1991 [DE] Germany .................. 41 37 698.6

[51] Int. Cl.$^6$ ...................................... C08G 77/06
[52] U.S. Cl. .................. 528/18; 528/34; 528/38; 524/588; 524/864
[58] Field of Search ...................... 524/588, 864; 528/18, 34, 38

[56] References Cited

U.S. PATENT DOCUMENTS

| | | | |
|---|---|---|---|
| 3,186,963 | 6/1965 | Lewis et al. | 260/46.5 |
| 3,678,003 | 7/1972 | Kaiser et al. | 260/46.5 G |
| 3,927,052 | 12/1975 | Vizurraga | 260/429.7 |
| 4,101,499 | 7/1978 | Herzig | 260/37 SB |
| 4,102,860 | 7/1978 | Wohlfarth et al. | 528/18 |
| 4,191,817 | 3/1980 | Schiller et al. | 528/38 |
| 4,460,761 | 7/1984 | Schiller et al. | 528/18 |
| 4,462,936 | 7/1984 | Hechtl et al. | 260/429.7 |
| 4,490,500 | 12/1984 | Smith | 524/378 |

FOREIGN PATENT DOCUMENTS

| | | |
|---|---|---|
| 0304958 | 3/1989 | European Pat. Off. . |
| 1167527 | 4/1964 | Germany . |

*Primary Examiner*—Karen A. Dean
*Attorney, Agent, or Firm*—Martin Connaughton

[57] ABSTRACT

The compositions proposed contain, as their main constituents, (a) a diorganopolysiloxane with triorganosiloxy groups as terminal groups, the organic groups being hydrocarbon groups which may be halogenated, (b) the reaction product of a diacylated diorganotin compound with a disilaalkane containing, per molecule, at least two monovalent hydrocarbon groups which are bonded to silicon via oxygen and may optionally be substituted by an alkoxy group, or with an oligomer of such a disilaalkane, (c) an organosilicon compound containing, per molecule, at least one amino or amino group bonded to silicon via carbon, (d) optionally, a filler and (e) optionally, a disilaalkane and/or silane containing, per molecule, at least three monovalent hydrocarbon groups which are bonded to silicon via oxygen and may optionally be substituted by an alkoxy group, or an oligomer of such a disilaalkane and/or silane.

6 Claims, No Drawings

TIN COMPOUND-CONTAINING COMPOSITIONS AS ONE OF THE TWO COMPONENTS OF TWO COMPONENT SYSTEMS WHICH CROSSLINK AT ROOM TEMPERATURE TO GIVE ORGANOPOLYSILOXANE ELASTOMERS

U.S. Pat. No. 4,490,500 (published 25 Dec. 1984, R. A. Smith, General Electric Co.) has already disclosed tin compound-containing compositions as one of the two components of two-component systems which crosslink at room temperature to give organopolysiloxane elastomers. According to the abovementioned publication, a composition of this type is prepared, for example, by mixing (1) the product of the reaction of tetraethyl silicate with dibutyltin dilaurate with (2) gamma-aminopropyltriethoxysilane, (3) pyrogenically produced silicon dioxide which has been treated with hexamethyldisilazane, (4) calcium carbonate and (5) dimethylpolysiloxane containing vinyl terminal groups.

EP-A 304 958 (laid open on 1 Mar. 1989, M. Fukayama et al., Toray Silicone Co.) likewise describes tin compound-containing compositions as one of the two components of two-component systems which crosslink at room temperature to give organopolysiloxanes, for example mixtures of (1) 1,2-bis(triethoxysilyl)ethane, (2) a product of the reaction of gamma-aminopropyltrimethoxysilane and gamma-glycidoxypropyltrimethoxysilane and (3) dibutyltin dilaurate.

The object was to provide tin compound-containing compositions as one of the two components of two-component systems which crosslink at room temperature to give organopolysiloxane elastomers, which compositions are not too complex to prepare and which, even without solvents, are homogeneous, flexible and soft, and have self-levelling to non-slump properties, the latter thus not spreading further, without mechanical treatment, on surfaces to which they have been applied, may be transparent to black, and still have all these properties even after relatively long storage at low or high ambient temperatures, giving after mixing with the other components of two-component systems which crosslink at room temperature to give organopolysiloxane elastomers, elastomers which are particularly resistant to weathering, steam and hot water and have excellent adhesion, even without prior priming, to a very wide variety of materials, not only of a silicate nature, such as glass, but also to metals and plastics, and the pot life, i.e. the time which passes between commencement of mixing of the two components with one another and significant crosslinking, and the properties of the elastomers obtained after mixing and crosslinking only changing a little, or not at all, even after relatively long storage of the compositions before this mixing and even irrespective of the crosslinking temperature. This object is achieved by the invention.

The invention relates to tin compound-containing compositions as one of the two components of two-component systems which crosslink at room temperature to give organopolysiloxane elastomers, the compositions containing, as essential constituents (a) a diorganopolysiloxane which contains triorganosiloxy groups as terminal units and in which the organic radicals are hydrocarbon radicals, which may be halogenated, (b) a product of the reaction of a disilaalkane containing at least two monovalent hydrocarbon radicals per molecule which are bonded to silicon via oxygen and are optionally substituted by an alkoxy group, or an oligomer thereof, with a diorganotin diacylate, (c) an organosilicon compound containing at least one amino or imino group per molecule which is bonded to silicon via carbon, if desired (d) a filler and if desired (e) a disilaalkane and/or silane containing at least three monovalent hydrocarbon radicals per molecule which are bonded to silicon via oxygen and are optionally substituted by an alkoxy group or an oligomer thereof.

The diorganopolysiloxane (a) containing triorganosiloxy groups as terminal units is preferably one of the formula

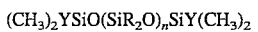

$(CH_3)_2YSiO(SiR_2O)_nSiY(CH_3)_2$ where the radicals R are identical or different hydrocarbon radicals having 1 to 8 carbon atoms per radical, it being possible for these radicals to be halogenated, Y is a methyl or vinyl group, and n is a positive integer having a value such that the mean viscosity of the diorganopolysiloxane (a) used in each case is from 1000 to 100,000 mPa.s at 25° C., in particular from 1000 to 50,000 mPa.s at 25° C.

Examples of hydrocarbon radicals in the diorganopolysiloxanes (a), and thus also of hydrocarbon radicals R, are alkyl radicals, such as the methyl, ethyl, n-propyl, isopropyl and 2-ethylhexyl radicals; hydrocarbon radicals containing aliphatic carbon-carbon double bonds, such as the vinyl radical; cycloalkyl radicals, such as the cyclohexyl and methylcyclohexyl radicals; aryl radicals, such as the phenyl radical; alkaryl radicals, such as tolyl radicals; and aralkyl radicals, such as the benzyl radical.

Examples of halogenated hydrocarbon radicals in the diorganopolysiloxanes (a), and thus also of halogenated hydrocarbon radicals R, are, in particular, fluorinated hydrocarbon radicals, such as the 3,3,3-trifluoropropyl radical and difluorophenyl radicals.

The organic radicals in the diorganopolysiloxanes (a), and thus the radicals R and Y, are particularly preferably methyl radicals.

Diorganopolysiloxanes (a) are known and commercially available.

The compositions according to the invention may contain one type of diorganopolysiloxane (a). However, they may also contain a mixture of at least two different types of such organopolysiloxanes.

Products of the reaction of a silane containing at least two monovalent hydrocarbon radicals per molecule which are bonded to silicon via oxygen and are optionally substituted by an alkoxy group, or an oligomer thereof, with a diorganotin diacylate are known, as is the preparation of reaction products of this type. In this respect, reference may be made, in addition to the U.S. patent mentioned at the outset, to, for example, DE-B11 67 527, published on 9 Apr. 1964, Farbenfabriken Bayer Aktiengesellschaft; U.S. Pat. No. 3,186,963, published 1 Jun. 1965, I. T. Lewis et al., Midland Silicones Limited; U.S. Pat. No. 3,927,052 published 16 Dec. 1975, L. R. Vizzuraga, Fibers Industries Inc.; U.S. Pat. No. 4,102,860, published 25 Jul. 1978, E. Wolfahrt et al., Wacker-Chemie GmbH; U.S. Pat. No. 4,460,761, published 17 Jun. 1984, A. Schiller et al., Wacker-Chemie GmbH; and U.S. Pat. No. 4,462,936, published 31 Jul. 1984, W. Hechtl et al., Wacker-Chemie GmbH.

The preparation of the reaction products (b) according to the invention from a disilaalkane or an oligomer thereof and a diorganotin diacylate is carried out analogously to the abovementioned preparation of the products of the reaction of a silane or an oligomer thereof with a diorganotin diacylate.

The disilaalkanes used for the preparation of the reaction products (b) and containing at least two monovalent hydrocarbon radicals per molecule which are bonded to silicon via oxygen and are optionally substituted by an alkoxy group are those of the formula $$(R^1O)_{3-a}Si\underset{\underset{R_a}{|}}{}-R^2-\underset{\underset{R^3_b}{|}}{}Si(OR^4)_{3-b}$$

in which R is as defined above, $R^3$ is as defined for R, $R^1$ and $R^4$ are monovalent hydrocarbon radicals having 1 to 8 carbon atoms per radical which are optionally substituted by an alkoxy group, $R^2$ is an unsubstituted or substituted divalent hydrocarbon radical having 1 to 10 carbon atoms per radical, and a and b are 0, 1 or 2, preferably 0 or 1, or oligomers thereof.

The radicals R and $R^3$, and $R^1$ and $R^4$ may be identical or different.

All comments on and examples of the radicals R in the organopolysiloxanes (a) also apply to the radicals R and $R^3$ in the abovementioned formula.

If $R^1$ and $R^4$ are hydrocarbon radicals, they are preferably alkyl radicals having 1 to 4 carbon atoms per radical, such as the methyl, ethyl, n-propyl, isopropyl, n-butyl and sec.-butyl radicals, or a mixture of at least two different radicals of this type.

Examples of hydrocarbon radicals $R^1$ and $R^4$ which are substituted by an alkoxy group are those of the formulae $CH_3O(CH_2)_2-$ $CH_3CH_2O(CH_2)_2-$ $CH_3OCH_2(CH_3)HC-$ and $CH_3OCH(CH_3)H_2C-$.

Examples of unsubstituted radicals $R^2$ are those of the formulae $-(CH_2)_2-$, $-(CH_2)_3-$, $-(CH_2)_4-$ and $-(CH_2)_8-$.

Examples of substituted radicals $R^2$ are those of the formulae $-CH(CH_3)CH_2-$, $-CH_2CH(CH_3)CH_2CH_2-$ and $-CH_2CH(C_2H_5)(CH_2)_4-$.

Oligomers of disilaalkanes of the abovementioned formula are taken to mean those compounds which are: obtainable, for example, by partial hydrolysis of disilaalkanes containing at least 2 and at the most 10 silicon atoms linked to one another by siloxane oxygen and containing on average at least 0.5 $R^1O-$ and $R^4O-$ groups per silicon atom.

Individual examples of disilaalkanes, or oligomers thereof, from which the reaction products (b) can be prepared by reaction with a diorganotin diacylate are 1,1-bis(trimethoxysilyl)ethane, 1,2-bis(trimethoxysilyl)ethane, 1,1-bis(methyldimethoxysilyl)ethane 1,1-bis(triethoxysilyl)ethane, 1,2-bis(triethoxysilyl) ethane, 1,2-bis(triethoxysilyl)propane, 1-(triethoxysilyl)-2-(methyl-diethoxysilyl)ethane and 1,3-bis(2-triethoxysilylethyl)tetraethoxydisiloxane.

It is possible to employ one type of disilaalkane of the type defined above under (b), or an oligomer thereof, in the preparation of the reaction products (b) by reaction with a diorganotin diacylate. However, it is also possible to use a mixture of at least two different silicon compounds of this type, for example a mixture of 1,2-bis(triethoxysilyl)ethane and 1,2-bis(trimethoxysilyl)ethane, in the preparation of the reaction products (b).

Preferred diorganotin diacylates are those of the formula $R_2Sn(OOCR^5)_2$ in which R is as defined above, and the $R^5$ radicals are identical alkyl radicals having 1 to 12 carbon atoms per radical. The examples of alkyl radicals R also apply fully to the radicals $R^5$.

Individual examples of diorganotin diacylates by whose reaction with a disilaalkane and/or an oligomer thereof of the type defined above under (b) the reaction products (b) can be prepared are di-n-butyltin diacetate, di-n-butyltin dilaurate and di-2-ethylhexyltin diacetate.

It is possible to employ one type of diorganotin diacylate or a mixture of at least two different types of diorganotin diacylate in the preparation of the reaction products (b).

The silicon compounds defined above under (b), and thus also the disilaalkanes of the abovementioned formula or oligomers thereof, are preferably employed in the preparation of the reaction products (b) in amounts of from 4 to 25 gram equivalents of $R^1O-$ and $R^4O-$ groups per gram mole of diorganotin diacylate.

The compositions according to the invention preferably contain reaction products (b) in amounts of from 0.01 to 1 per cent by weight of tin, in particular from 0.05 to 0.5 per cent by weight of tin, in each case based on the total weight of the particular composition.

The organosilicon compounds (c) containing at least one amino or imino group bonded to silicon via carbon are preferably silanes which contain in each molecule at least one amino group or imino group bonded to silicon via carbon and at least one monovalent hydrocarbon radical bonded to silicon via carbon and is optionally substituted by an amino or alkoxy group, and siloxanes containing at least one amino or imino group per molecule bonded to silicon via carbon. Organosilicon compounds (c) of this type are disclosed, for example, in U.S. Pat. No. 3,678,003, published 18 Jul. 1972, W. Kaiser et al., Wacker-Chemie GmbH, and U.S. Pat. No. 4,191,817, published 4 Mar. 1980, A. Schiller et al., Wacker-Chemie GmbH. It is possible to use any desired organosilicon compounds which are mentioned in these two publications or come under the formulae given in these two publications, if they come under the definition of the organosilicon compounds (c) of the present invention, during the treatment of the compositions according to the invention.

Individual examples of silanes of the above-defined type are those of the formulae $CH_3Si[O(C_2)_2NH_2]_2$
$(CH_2)_3O(CH_2)_2N_2(CH_3O)_3Si(CH_2)_3NH(CH_2)_2NH_2H_2N(CH_2)_2$
$O(CH_2)_3Si(OCH_2CH_2NH_2)_3H_2N(CH_2)_2O(CH_2)_3Si(OC_2H_5)_3$ and compounds with the names gamma-aminopropyltriethoxysilane, aminomethyltriethoxysilane, 3-(2-aminoethylamino)propyltri-n-propoxysilane and delta-aminobutyltriethoxysilane.

An important individual example of an organopolysiloxane containing at least one amino or imino group per molecule bonded to silicon via carbon is a product of the reaction of the silane of the formula $H_2N(CH_2)_2NH(CH_2)_3Si(OCH_3)_3$ with a dimethylpolysiloxane containing one Si-bonded hydroxyl group in each of the terminal units and having a viscosity of 80 mPa.s at 25° C.

The compositions according to the invention preferably contain the organosilicon compound (c) in amounts of from 1 to 30 per cent by weight, in particular from 5 to 20 per cent by weight, in each case based on the total weight of the particular composition.

The compositions according to the invention may contain reinforcing and/or non-reinforcing fillers (d). The compositions according to the invention preferably contain reinforcing fillers.

The reinforcing filler (d), i.e. a filler having a specific surface area of at least 50 m²/g, is preferably silicon dioxide. The reinforcing filler (d) is preferably silicon dioxide having a specific surface area of from 100 to 400 m²/g, in particular from 120 to 300 m²/g. The reinforcing filler (d) is particularly preferably pyrogenically produced silicon dioxide. If desired, however, the reinforcing filler (d) may be a silicic acid hydrogel which has been dewatered with retention of the structure, i e a so-called "aerogel", or another type of precipitated silicon dioxide having a specific surface area of at least 50 m²/g.

The values indicated here in the description for the specific surface area of silicon dioxide or other fillers are BET values, i.e. values determined by nitrogen adsorption in accordance with ASTM Special Technical Publication No. 51, 1941, page 95 ff.

The reinforcing filler (d) is preferably employed in amounts of from 10 to 50 per cent by weight, based on the weight of the amount of organopolysiloxane (a) used in each case.

The reinforcing filler, preferably silicon dioxide having a specific surface area of at least 50 m²/g, particularly preferably pyrogenically produced silicon dioxide, is preferably hydrophobicised before use in the compositions according to the invention by reaction with an organosilicon compound.

The organosilicon compound by means of which the reinforcing filler, in particular silicon dioxide, is hydrophobicised is preferably one of the formula $(R_3Si)_mX$, in which R is as defined above, X is halogen, OH, OR¹ (R¹ is as defined above), S, OOCR⁶ (R⁶=a hydrocarbon radical having 1 to 4 carbon atoms) or NR⁷ (R⁷=hydrogen or is as defined for R⁶), and m is 1 or 2. Of these compounds, hexamethyldisilazane is particularly preferred.

The hydrophobicisation of the reinforcing filler (d), in particular silicon dioxide having a specific surface area of at least 50 m²/g, by reaction with an organosilicon compound is particularly preferably carried out in the presence of a diorganopolysiloxane (a) which contains triorganosiloxy groups as terminal units and in which the organic radicals are hydrocarbon radicals, which may be halogenated, and water with mechanical loading of the mixture at elevated temperature, water and excess organosilicon compounds used for the hydrophobicisation being removed after this hydrophobicisation from the mixture obtained from the hydrophobicisation. The process is disclosed, for example, in U.S. Pat. No. 4,101,499, published on 18 Jul. 1978, J. Herzig, Bayer Aktiengesellschaft. This hydrophobicisation and the subsequent removal of water and excess organosilicon compounds are naturally carried out before the resultant mixture is mixed with the other constituents of the compositions according to the invention. In the hydrophobicisation, water is preferably used in amounts of from 0.1 to 20 per cent by weight, in particular from 2 to 10 per cent by weight, in each case based on the amount by weight of diorganopolysiloxane (a) present during hydrophobicisation.

The compositions according to the invention may also contain non-reinforcing fillers.

Examples of non-reinforcing fillers (d), i.e. fillers having a specific surface area of less than 50 m²/g, are carbon black, quartz sand, Neuburg siliceous chalk, diatomaceous earth, calcium silicate, zirconium silicate, calcium carbonate and aluminiumoxide, it being possible for these non-reinforcing fillers to have organosilyl groups on their surface or to have been pretreated in another manner, and organic polymers in fibrous or pulverulent form, such as polyvinyl chloride powder. Calcium carbonate is particularly preferred.

If a disilaalkane containing only two monovalent hydrocarbon radical per molecule which are bonded to silicon via oxygen and are optionally substituted by an alkoxy group or containing not more than 8 gram equivalents of monovalent hydrocarbon radicals which are bonded to silicon via oxygen and are optionally substituted by an alkoxy group per gram mole of diorganotin diacylate was used in the preparation of the reaction product (b), the compositions according to the invention must thus also contain (e) a disilaalkane and/or silane containing at least three monovalent hydrocarbon radicals per molecule which are bonded to silicon via oxygen and are optionally substituted by an alkoxy group, or an oligomer thereof.

All comments on and examples of disilaalkanes used for the preparation of the reaction product (b), as long as they contain more than two hydrolysable radicals per molecule, also apply to the disilaalkanes (e).

In addition to a disilaalkane, the compositions according to the invention may optionally contain a silane containing at least three monovalent hydrocarbon radicals per molecule which are bonded to silicon via oxygen and are optionally substituted by an alkoxy group, or an oligomer thereof. Silanes of the formula $R_cSi(OR^1)_{4-c}$, in which R is as defined above, the R¹ radicals are monovalent hydrocarbon radicals having 1 to 8 carbon atoms per radical which are optionally substituted by an alkoxy group, and c is 0 or 1, or oligomers thereof, are preferred.

All comments on and examples of the radicals R in the organopolysiloxanes (a) and R¹ in the disilaalkanes also apply to the radicals R and R¹ in the abovementioned formula.

Individual examples of silanes or oligomers thereof are tetraethoxysilane, tetra-n-butoxysilane, vinyltriethoxysilane, dimethyldiethoxysilane, hexaethoxydisiloxane and ethoxypolysiloxanes having an SiO₂ content of from 30 to 45 per cent by weight, for example a product commercially available under the name "Ethylsilikat 40".

The compositions according to the invention preferably contain organosilicon compounds (e) in amounts of from 5 to 10 per cent by weight, in particular from 10 to 30 per cent by weight, in each case based on the total weight of the particular composition.

It may be noted in this connection that the sum of the percentages actually selected in the amount ranges indicated here must of course add up to 100.

The SiOC-bonded radicals in constituents (b), (c) and (e) are preferably in each case identical.

In addition to constituents (a), (b), (c) and preferably (d) and (e), the compositions according to the invention may optionally contain further substances, provided that these substances are inert towards the constituents mentioned above and are suitable as additives in tin compound-containing compositions as one of the two components of two-component systems which crosslink at room temperature to give organopolysiloxane elastomers. Examples of such substances are, in particular, those which are defined above under (a), but contain no reinforcing fillers (d), in particular silicon dioxide, before their addition to the compositions. Their amount is preferably at most 80 per cent by weight, based on the total weight of the particular composition. Further examples of substances which are inert towards the other constituents of the compositions according to the invention and which may additionally be present in the compositions according to the invention are pigments, such as carbon black, titanium dioxide and iron oxide, soluble dyes, fragrances, thixotropic agents, such as hydrogenated castor oil, and reinforcing fillers, such as silicon dioxide having a surface area of at least 50 m²/g, which has particularly preferably been reacted with an organopolysiloxane of the type defined aboveunder (a) with an organosilicon compound, such as hexamethyldisilazane, or another compound which comes under the formula indicated above in connection with the hydrophobicisation of reinforcing fillers (d), so completely that it contains no silanol groups.

The component other than the tin compound-containing composition, with which the tin compound-containing composition is mixed in order to give a composition which crosslinks at room temperature to give an organopolysiloxane elastomer, may of course contain the same constituents as it was also possible for other components of this type to contain hitherto. These are, in particular, the diorganopolysiloxanes to be cross-linked, usually those which may be reproduced by the formula

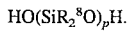

HO(SiR₂⁸O)ₚH.

In this formula, the radicals $R^8$ are identical or different monovalent SiC-bonded organic radicals, and p is an integer having a value of at least 10.

Within and/or along the siloxane chain of the abovementioned formula for diorganopolysiloxanes containing one Si-bonded hydroxyl group in each of the terminal units, other siloxane units may also be present in addition to the diorganosiloxane units ($SiR_2^8O$), which is usually not shown in formulae of this type. Examples of other siloxane units of this type, which are, however, usually only present as impurities which are more or less difficult to avoid, are those of the formulae $R^8SiO_{3/2}$, $R_3^8SiO_{1/2+cc}$ and $SiO_{+c,fra\ 4/2}$, where $R^8$ is in each case as defined above. However, the amount of other siloxane units of this type should not exceed 1% of the number of siloxane units present in these diorganopolysiloxanes. Still other additional siloxane units, such as those of the formula —OSiR₂⁸R⁹SiR₂⁸O—, in which $R^8$ is as defined above, and $R^9$ is a divalent hydrocarbon radical, for example the phenylene radical, may also be present in relatively large amounts.

Examples of organic radicals $R^8$ are hydrocarbon radicals, such as alkyl radicals, for example the methyl, ethyl, n-propyl, isopropyl, butyl, hexyl and octadecyl radical; radicals containing aliphatic carbon-carbon double bonds, such as the vinyl, allyl, ethylallyl and butadienyl radicals; aryl radicals, such as the phenyl radical; alkaryl radicals, such as tolyl radicals; and aralkyl radicals, such as the beta-phenylethyl radical.

These hydrocarbon radicals my be substituted, in particular halogenated, such as the 3,3,3-trifluoropropyl, chlorophenyl and bromotolyl radicals. Other examples of organic radicals $R^8$ are cyanoalkyl radicals, such as the beta-cyanoethyl radical.

These organopolysiloxanes containing one Si-bonded hydroxyl group in each of the terminal units may be in the form of a mixture with polymers, produced in their presence by polymerisation or copolymerisation by means of free radicals, of compounds which can be polymerised by addition polymerisation, such as styrene, vinyl acetate, acrylic acid, methacrylic acid, acrylates, methacrylates or acrylonitrile, or a mixture of at least two polymerisable compounds of this type, such as a mixture of styrene and n-butyl acrylate. These polymers need not all be mixed with the diorganopolysiloxanes. Rather, they may be grafted onto the diorganopolysiloxane, at least to a slight extent.

At least the majority of the radicals $R^8$ (if no polymer is grafted on) preferably comprises methyl radicals, in particular due to the ready accessibility. Any other radicals $R^8$ which may be present are, in particular vinyl radicals or phenyl radicals or vinyl and phenyl radicals.

The viscosity of the organopolysiloxanes to be crosslinked is preferably from 100 to 500,000 mPa.s at 25° C.

Before the organopolysiloxanes to be crosslinked are mixed with the compositions according to the invention, they may contain not only, if appropriate, the abovementioned polymers produced in their presence, but may also contain substances which are inert toward these polymers, at least at room temperature, and which are conventional constituents of compositions which can be cured to give organopolysiloxane elastomers. Examples of substances of this type are reinforcing fillers, non-reinforcing fillers, pigments, soluble dyes, fragrances, corrosion inhibitors, oxidation inhibitors, heat stabilisers, peroxides, organopolysiloxane resins comprising $(CH_3)_3SiO_{1/2}$ and $SiO_{4/2}$ units, such 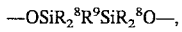 organopolysiloxane resins preferably in amounts of at most 1 per cent by weight, based on the weight of the organopolysiloxane to be crosslinked, purely organic resins produced in the absence of the diorganopolysiloxanes, such as polyvinyl chloride powders, and plasticizers, such as the organopolysiloxanes defined above under (a), and polyglycols, which may be etherified and/or esterified, including organopolysiloxane-oxyalkylene block copolymers.

Examples of reinforcing fillers, which my be in the form of a mixture with the organopolysiloxanes to be crosslinked, before or when they are mixed with the composition according to the invention, are pyrogenically produced silicon dioxide having a specific surface area of at least 50 m²/g, aerogels or another precipitated silicon dioxide having a specific surface area of at least 50 m²/g. These fillers may, at least in part, have organosilyl groups on their surface.

The examples of non-reinforcing fillers already mentioned somewhat further above also apply fully to the non-reinforcing fillers which may be in the form of a mixture with the organopolysiloxanes to be crosslinked, before or when these are mixed with the composition according to the invention.

The compositions according to the invention are mixed with the other components of the particular two-component system which crosslinks at room temperature to give an organopolysiloxane elastomer and whose first component contains a tin compound, in such amounts that the ratio between the organopolysiloxane to be cross-linked and the compound as defined above under (e) and tin in the resultant finished mixture is the usual one in two-component systems which crosslink at room temperature to give organopolysiloxane elastomers and whose first component is a tin compound, the amount of tin, calculated as the element, preferably being from 10 to 1000 ppm by weight, in particular from 50 to 500 ppm by weight, in each case based on the total weight of the finished mixture.

The compositions according to the invention are preferably employed in amounts of from 1 to 20 per cent by weight, in particular from 5 to 15 per cent by weight and particularly preferably from 10 to 15 per cent by weight, based on the amount of the other component used in each case.

The compositions obtained by mixing the composition according to the invention with the other component of two-component systems which crosslink at room temperature to give organopolysiloxane elastomers can be employed for any desired purposes for which it is possible to employ two-component systems which crosslink at room temperature to give organopolysiloxane elastomers and whose first component contains a tin compound. These purposes are, for example, for use as adhesives in the electrical, electronics, automotive and aircraft industries, for sealing joints and similar gaps in above-ground and underground construction, for bonded glazing (structural glazing), i.e. for a type of construction in which the transparent or opaque glass panes or glass elements are adhesively bonded to one another or bonded to the frames, as an edge bonding material in the production of insulating glass units, and for the production of protective coatings.

In the examples below, all part and percentage data relate to the weight, unless otherwise specified.

In the examples below, the statement that a paste has non-slump properties means that it emerges by not more than 2 mm from a vertical rail having a profile with the dimensions width 20 mm±0.2 mm, depth 10 mm±0.2 mm when tested in accordance with EN (Euro Norm) 27390.

EXAMPLE 1 a) 100 parts of a dimethylpolysiloxane containing one vinyl group in each of the terminal units and having a viscosity of 20,000 mPa.s at 25° C. are mixed with 19 parts of hexamethyldisilazane and 7 parts of water in a trough compounder under nitrogen and agitated in the compounder for 15 minutes at room temperature to give a uniform mixture. The resultant mixture is mixed in the compounder with 63 parts of a silicon dioxide produced pyrogenically in the gas phase and having a specific surface area of 300 m$^2$/g. The resultant mixture is compounded first for one hour at room temperature and then for 2 hours at 100° C. The pressure in this compounder is then reduced to 80 hPa (abs.) by sucking the gaseous contents out of the compounder, and the remaining compounder contents are warmed to 140° C. and heated at this temperature for 2 hours. After cooling to room temperature and venting, 100 parts of the resultant mixture are diluted with 30 parts of the dimethylpolysiloxane containing one vinyl group in each of the terminal units and having a viscosity of 20,000 mPa.s at 25° C.

b) A mixture of 3 parts of bis(triethoxysilyl)ethane and 1 part of di-n-butyltin diacetate is warmed at 120° C. for six hours with stirring under the pressure of the ambient atmosphere. At the same time, the ethyl acetate formed is constantly removed by distillation. The valence vibration of the carboxyl group of di-n-butyltin diacetate, which is at 1600 cm$^{-1}$, has then disappeared in the infra-red spectrum.

c) 72.2 parts of the mixture whose preparation is described above under a) in this example are mixed in a planetary mixer first with 18 parts of bis(triethoxysilyl)ethane, then with 6 parts of 3-aminopropyltriethoxysilane and finally with 3.3 parts of the reaction product whose preparation is described above under b) in this example, at room temperature and under the pressure of the ambient atmosphere.

Finally, gaseous constituents of the composition, which form bubbles in the composition, are removed by reducing the pressure in the compounder.

A transparent, homogeneous, flexible, soft past with non-slump properties is obtained. These properties or the paste do not change even after storage for 7 days at 70° C. or for 2 months at 50° C., in each case in a tin tube sealed in an air-tight manner.

EXAMPLE 2 a) The procedure described in Example 1 under b) is repeated, with the difference that 4 parts of bis(trimethoxysilyl)ethane are employed instead of 3 parts of bis(triethoxysilyl)ethane, methyl acetate instead of ethyl acetate being removed by distillation.

b) 50 parts of a dimethylpolysiloxane containing one vinyl group in each of the terminal units and having a viscosity of 20,000 mPa.s at 25° C. are mixed at room temperature and under the pressure of the ambient atmosphere in a planetary mixer with 15 parts of carbon black having a specific surface area of 45 m$^2$/g. 25.5 parts of bis(trimethoxysilyl)ethane, 9 parts of 3-(2-aminoethyl)aminopropyltrimethoxysilane and 0.5 part of the reaction product whose preparation is described under a) in this example are then stirred in, likewise at room temperature and under the pressure of the ambient atmosphere. Finally, gaseous constituents of the composition, which form bubbles in the composition, are removed by reducing the pressure in the compounder.

A black, homogeneous, flexible, soft paste with non-slump properties is obtained. The properties of this paste do not change even after storage for 7 days at 70° C. or for 2 months at 50° C., in each case in a tin tube sealed in an air-tight manner.

Comparative Experiment V1 a) A mixture of 3.5 parts of tetraethoxysilane and 1 part of di-n-butyltin dilaurate is warmed at 140° C. for 2 hours with stirring under the pressure of the ambient atmosphere. The valence vibration of the carbonyl group of di-n-butyltin dilaurate, which is at 1600 cm$^{-1}$, has then disappeared in the IR spectrum trum.

b) 26 parts of a dimethylpolysiloxane containing one vinyl group in each of the terminal units and having a viscosity of 20,000 mPa.s at 25° C. are mixed in a planetary mixer first with 24 parts of calcium carbonate having a specific surface area of 2.5 m$^2$/g, then with 12 parts of a hydrophobic silicic acid having a specific surface area of 140 m$^2$/g and a carbon content of 2.5 %, at room temperature and under the pressure of the ambient atmosphere. 12.7 parts of tetraethoxysilane, 24 parts of 3-aminopropyltriethoxysilane and 1.3 parts of the reaction product whose preparation is described under a) in this example are subsequently stirred in one after the other, likewise at room temperature and under the pressure of the ambient atmosphere. Finally, gaseous constituents of the composition, which form bubbles in the composition, are removed by reducing the pressure in the compounder.

A white, homogeneous, flexible, soft paste with non slump properties is obtained. These properties do not change even after storage for 7 days at 70° C. or for 2 months at 50° C., in each case in a tin tube sealed in an air-tight manner.

Comparative Experiment V2 a) 22 parts of 3-aminopropyltriethoxysilane and 50 parts of 3-glycidoxypropyltrimethoxysilane are homogeneously mixed with one another at room temperature and under the pressure of the ambient atmosphere, and the mixture is then left to stand for 7 days under the same conditions in the sealed vessel.

b) 75 parts of the mixture whose preparation is described under a) in Example 1 are mixed in a planetary mixing compounder first with 17.4 parts of bis(trimethoxysilyl)ethane, then with 7.3 parts of the reaction product whose preparation is described above under a) in this example, and finally with 0.3 part of di-n-butyltin dilaurate, at room temperature and under the pressure of the ambient atmosphere. Finally, gaseous constituents of the composition, which form bubbles in the composition, are removed by reducing the pressure in the compounder.

A transparent, homogeneous, flexible, soft paste with non-slump properties is obtained. After the paste has been stored for seven days at 70° C. or for two months at 50° C., in each case in a tin tube sealed in an air-tight manner, the paste was reassessed; its viscosity had increased. In addition, it had yellowed.

The examples below describe the use of the compositions whose preparation is described in Examples and 2 and Comparative Experiments 1 and 2 in two-component systems which crosslink at room temperature to give organopolysiloxane elastomers.

EXAMPLE 3

60 parts of a dimethylpolysiloxane containing one Si-bonded hydroxide group in each of the terminal units and having a viscosity of 75,000 mPa.s at 25° C. are mixed in a planetary mixing compounder first with 50 parts of a dimethylpolysiloxane which has been end-blocked by trimethylsiloxy groups and has a viscosity of 100 mPa.s at 25° C., then with 2 parts of 2,4,6-tri-n-butylphenol polyethylene glycol ether containing 13 ethylene oxide units per molecule, and finally with 90 parts of calcium carbonate whose surface is coated with stearic acid and which has a specific surface area of 20 $m^2/g$. Gaseous constituents of the composition, which can form bubbles in the composition, are subsequently removed by reducing the pressure in the compounder.

The resultant component other than the tin compound-containing component of a two-component system which crosslinks at room temperature to give an organopolysiloxane elastomer is homogeneous, flexible and soft and has non-slump properties. Each 100 parts of this other component are mixed with 10 parts of the pastes whose preparation is described under c) in Example 1 and under b) in Example 2 and under b) in the Comparative Experiments V1 and V2.

The results are shown in Tables I and II below. In these Tables, the notes have the following meanings:

1) The mechanical values of the elastomers were in each case determined on 1.5 to 2.2 mm thick films which were removed from the smooth, flat and greased substrate on which they had been produced after storage for 14 days at 23° C. and a relative atmospheric humidity of 50 %.
2) determined in accordance with DIN 53504 using an S3A standard bar (thickness variation of the bar: at most ±0.1 mm)
3) determined in accordance with DIN 53505
4) at 23° C. and a relative atmospheric humidity of 50%.

TABLE I[1]

| Tin compound-containing composition prepared as in Example or Comparative Experiment | Stored before use for | Crosslinking conditions | Processing time in min. | Tensile strength[2] σ max. [N/mm²] | Elongation at break[2] ε max. [%] | Stress at 100 % elongation[2] σ 100 [N/mm²] | Shore A hardness[3] |
|---|---|---|---|---|---|---|---|
| 1 c | — | 4) | 16 | 1.9 | 510 | 0.51 | 26 |
| 1 c | 7 days at 70° C. | 4) | 20 | 1.9 | 520 | 0.51 | 28 |
| 1 c | 2 months at 50° C. | 4) | 50 | — | — | — | — |
| 2 b | — | 4) | 17 | 1.4 | 370 | 0.45 | 23 |
| 2 b | 7 days at 70° C. | 4) | 24 | 1.5 | 450 | 0.42 | 25 |
| 2 b | 2 months at 50° C. | 4) | 19 | — | — | — | — |
| V1 | — | 4) | 27 | 0.45 | 380 | 0.20 | 13 |
| V1 | 7 days at 70° C. | 4) | 34 | 0.52 | 510 | 0.15 | 13 |
| V1 | 2 months at 50° C. | 4) | 58 | — | — | — | — |
| V2 | — | 4) | 56 | 2.2 | 710 | 0.41 | 25 |
| V2 | 7 days at 70° C. | 4) | 120 | 2.1 | 700 | 0.40 | 25 |
| V2 | 2 months at 50° C. | 4) | 300 | — | — | — | — |

TABLE II

Resistance of the elastomers[1] prepared as described in Examples 1 c and 2 b and Comparative Experiments V1 and V2 to water vapour at 70° C.:

| | Example or Comparative Experiment | | | | | | | | | | | |
|---|---|---|---|---|---|---|---|---|---|---|---|---|
| | 1 c | | | 2 b | | | V1 | | | V3 | | |
| Mech. values | +) | ++) | +++) | +) | ++) | +++) | +) | ++) | +++) | +) | ++) | +++) |
| Tensile strength[2] N/mm² | 1.9 | 0.82 | 0.49 | 1.4 | 0.60 | 0.40 | 0.45 | depolymerised | | 2.2 | 1.6 | 1.3 |
| Elongation at break[2] % | 510 | 620 | 470 | 370 | 670 | 620 | 380 | depolymer- | | 710 | 590 | 660 |

TABLE II-continued

Resistance of the elastomers[1] prepared as described in Examples 1 c and 2 b and Comparative Experiments V1 and V2 to water vapour at 70° C.:

| | Example or Comparative Experiment | | | | | | | | | | | |
|---|---|---|---|---|---|---|---|---|---|---|---|---|
| | 1 c | | | 2 b | | | V1 | | | V3 | | |
| Mech. values | +) | ++) | +++) | +) | ++) | +++) | +) | ++) | +++) | +) | ++) | +++) |
| Stress at 100% elongation[2] N/mm² | 0.51 | 0.37 | 0.23 | 0.45 | 0.30 | 0.20 | 0.20 | ised depolymer-ised | | 0.41 | 0.30 | 0.22 |
| Shore A hardness[3] | 26 | 19 | 15 | 23 | 14 | 12 | 13 | depolymer-ised | | 25 | 21 | 15 |

+) After crosslinking[4] and storage[1]
++) After crosslinking[4] and storage[1] with subsequent storage for two weeks at 70° C. and relative atmospheric humidity of 100%
+++) After crosslinking[4] and storage[1] and subsequent storage for eight weeks at 70° C. and relative atmospheric humidity of 100%

EXAMPLE 4

The composition which crosslinks to give an elastomer and whose preparation is described above under Example 3 is allowed to crosslink in extrudate form on the substrates indicated in Table III, these substrates being unprimed and having been degreased by means of solvents before application of the extrudates. The results of testing for adhesion to the substrates are given in Table III.

Key to Table:

A) after 7 days from application of the extrudate to the substrate and subsequent storage of the resultant arrangement at 23° C. and relative atmospheric humidity of 50%

B) after 7 days from application of the extrudate to the substrate, subsequent storage of the resultant arrangement at 23° C. and 50% relative atmospheric humidity and subsequent storage of the arrangement for 14 days under water at 60° C.

c) after 7 days from application of the extrudate to the substrate, subsequent storage of the resultant arrangement at 23° C. and 50% relative atmospheric humidity and subsequent storage of the arrangement for 28 days under water at 60° C.

+ good adhesion=cohesive fracture=crack in the elastomer

φ moderate adhesion=adhesive fracture and cohesive fracture=separation from the substrate and crack in the elastomer − poor adhesion=adhesive fracture=separation from the substrate

TABLE III

Adhesion of the elastomer prepared using a tin compound-containing composition as in Example or Comparative Experiment

| | Example or Comparative Experiment | | | | | | | | | | | |
|---|---|---|---|---|---|---|---|---|---|---|---|---|
| | 1 c | | | 2 b | | | V1 | | | V2 | | |
| Substrate | A | B | C | A | B | C | A | B | C | A | B | C |
| Glass | + | + | + | + | + | φ | + | − | − | + | + | φ |
| Aluminium | + | + | + | + | + | + | + | − | − | − | φ | − |
| Anodically oxidised aluminium | + | + | + | + | + | + | − | − | − | − | φ | φ |
| Stainless steel | + | + | + | + | φ | + | + | − | − | − | + | + |
| Zinc plate | + | + | + | + | φ | + | + | − | − | − | + | φ |

TABLE III-continued

Adhesion of the elastomer prepared using a tin compound-containing composition as in Example or Comparative Experiment

| | Example or Comparative Experiment | | | | | | | | | | | |
|---|---|---|---|---|---|---|---|---|---|---|---|---|
| | 1 c | | | 2 b | | | V1 | | | V2 | | |
| Substrate | A | B | C | A | B | C | A | B | C | A | B | C |
| Rigid polyvinyl chloride | + | φ | + | + | φ | φ | − | − | − | − | − | − |

It can be seen from Tables I to III that the tin compound-containing compositions 1 c and 2 b, which contain the novel product of the reaction of a disilaalkane with a diorganodiacylate, have particularly good storage stability.

Mixing of in each case 10 parts of these compositions with 100 parts of the other component (base composition) gives compositions which, after crosslinking at room temperature, give elastomers which have particularly good mechanical strength, are particularly stable to hot water and steam and adhere particularly well to a very wide variety of materials, even when exposed to hot water.

We claim:

1. Tin compound-containing compositions as one of the two components of two-component systems which crosslink at room temperature to give organopolysiloxane elastomers, the compositions containing, as essential constituents (a) a diorganopolysiloxane which contains triorganosiloxy groups as terminal units and in which the organic radicals are hydrocarbon radicals, which are optionally halogenated, (b) a product of the reaction of a disilaalkane containing at least two monovalent hydrocarbon radicals per molecule which are bonded to silicon via oxygen and are optionally substituted by an alkoxy group, or an oligomer thereof, with a diorganotin diacylate, (c) an organosilicon compound containing at least one amino or imino group per molecule which is bonded to silicon via carbon, optionally (d) a filler and optionally (e) a disilaalkane and/or silane containing at least three monovalent hydrocarbon radicals per molecule which are bonded to silicon via oxygen and are optionally substituted by an alkoxy group or an oligomer thereof.

2. Compositions according to claim 1, characterised in that the SiOC-bonded organic radicals in the constituents (b), (c) and (e) are identical.

3. Tin compound-containing compositions as claimed in claim 1, wherein the diorganosiloxane (a) has the formula $$(CH_3)_2YSiO(SiR_2O)_nSiY(CH_3)_2$$

where

R are identical or different hydrocarbon radicals having from 1 to 8 carbon atoms per radical, Y is a methyl or vinyl group, and n is an integer having a value such that the mean viscosity of the diorganosiloxane is from 1000 to 100,000 mPa.s at 25° C.

4. Tin compound-containing compositions as claimed in claim 1, wherein the disilaalkane containing at least two monovalent hydrocarbon radicals which are bonded to silicon via oxygen has the formula $$(R^1O)_{3-a}\underset{\underset{R_a}{|}}{Si}-R^2-\underset{\underset{R^3_b}{|}}{Si}(OR^4)_{3-b}$$

where

R, $R^1$, $R^3$ and $R^4$ are identical or different hydrocarbon radicals having from 1 to 8 carbon atoms per radical optionally substituted by an alkoxy radical, $R^2$ is a substituted or unsubstituted divalent hydrocarbon radical having 1 to 10 carbon atoms per radical, and a and b are 0, 1 or 2.

5. Tin compound-containing compositions as claimed in claim 1, wherein the diorganotin diacylate has the formula $$R_2Sn(OOCR^5)_2$$

where

R is an identical or different hydrocarbon radical having from 1 to 8 carbon atoms per radical and $R^5$ is a hydrocarbon radical having from 1 to 12 carbon atoms per radical.

6. Tin compound-containing compositions as claimed in claim 1, wherein the organosilicon compound containing at least one amino or imino group per molecule is the product of a reaction of a silane of the formula $$H_2N(CH_2)_2NH(CH_2)_3Si(OCH_3)_3$$

with a dimethylpolysiloxane containing one Si-bonded hydroxyl group in each terminal unit and having a viscosity of 80 mPa.s at 25° C.

* * * * *